(12) United States Patent
Sankarasubbier et al.

(10) Patent No.: US 6,579,994 B2
(45) Date of Patent: Jun. 17, 2003

(54) PROCESS FOR PREPARATION OF 2-METHYL-1,4-NAPHTHOQUINONE

(75) Inventors: Narayanan Sankarasubbier; Katravulapalli V.V.S.B.S. Murthy; Kongara Madhusudan Reddy; Premchendar Nandhikonda, all of Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/821,783

(22) Filed: Mar. 29, 2001

(65) Prior Publication Data

US 2002/0188141 A1 Dec. 12, 2002

(51) Int. Cl.$^7$ .................. C07C 45/27; C07C 50/16; C07C 50/08; C07C 50/12
(52) U.S. Cl. ............... 552/208; 552/292; 552/295; 552/299
(58) Field of Search ................. 552/208, 292, 552/295, 299; 568/314, 315, 321, 328

(56) References Cited

U.S. PATENT DOCUMENTS 4,906,411 A  *  3/1990  Shinnaka et al.
5,637,741 A  *  6/1997  Matsumoto et al.

OTHER PUBLICATIONS

Chemical Abstract 375007 vol 88, No. 5, dated Jan. 1978 XP–002183396.

Arnold, R. T. et al., "Quinones by the Peroxide Oxidation of Aromatic Compounds" J. Organic Chemistry, vol. 5, 1940, pp. 250–252.

* cited by examiner

Primary Examiner—Samuel Barts
Assistant Examiner—Sikarl A. Witherspoon
(74) Attorney, Agent, or Firm—Ladas & Parry

(57) ABSTRACT

The present invention describes a process for the preparation of 2-Methyl-1,4-naphthoquinone by oxidizing 2-methylnaphthalene with hydrogen peroxide in the presence of acetic acid.

2 Claims, No Drawings

PROCESS FOR PREPARATION OF 2-METHYL-1,4-NAPHTHOQUINONE

FIELD OF THE INVENTION

The present invention relates to a process for the preparation of 2-Methyl-1,4-naphthoquinone (vitamin $K_3$, "menadione"). The present invention particularly relates to a process for producing 2-Methyl-1,4-naphthoquinone which is used as antihemoragic agent and in animal feed, by the oxidation of 2-Methylnaphthalene with hydrogen peroxide in the presence of acetic acid.

BACKGROUND OF THE INVENTION

Oxidation is one of the major and industrially important processes and widely 10 used in the synthesis of low and high volume chemicals and pharmaceutical industry. Furthermore, the traditional route of oxidation using mineral acids and inorganic oxides suffer from the disadvantages of high capital cost, reactor corrosion, formation of by product and the difficulty in the catalyst regeneration. In the recent times, scientists worldwide have been devoting their attention to the development of environmentally friendly catalysts and economically feasible routes.

Oxidation of arenes is important in chemical industries, especially in agrochemical and pharmaceutical industries. Many oxidation and hydroxylation reactions were studied using zeolites and redoxmolecular sieves (Sheldon et al. *Curr. Opin. Solid: State Mater. Sci.* 1, 1996, 101, Sheldon et al. *J. Mol. Catal.* A 107, 1996, 75; Kumar et al. *Synlett*. 1995, 289, Arends et al. *Angew. Chem. Int. Ed. Engl*. 36, 1997, 1145).

Oxidation of 2-Methylnaphthalene with a sulfuric acid solution of chromic acid was studied (Fieser, *J. Biol. Chem.*, 133, 1940, 391; Sheldon, *Top. Curr. Chem.*, 164, 1993, 21). However, in this stoichiometric oxidation about 18 kg of chromium containing waste is produced for 1 kg of product. Oxidation of 2-Methlynaphthalene was investigated in presence of acetic acid with hydrogen peroxide and methyl trioxo rhenium (Adam et al., *Angew. Chem. Int. Ed.*, 33, 1994, 2475; Herrmann et al., *J. Mol. Catal. A Chemical*, 138, 1999, 115). Oxidation of 2-Methylnaphthalene was carried over Pd-polystyrenesulfonic acid resin in the acetic acid with hydrogen peroxide (Yamaguchi et al., *Chem. Lett.*, 1985, 827). Metalloporphyrin catalyzed oxidation of 2-Methylnaphthalene by potassium monopersulfate was studied (Song et al, *J. Org. Chem.*, 62, 1997, 673). The oxidation of 2-Methylnaphthalene has been carried out using ammonium persulfate as an oxidizing agent in the presence of cerium (IV) ammonium sulfate and silvernitrate in an emulsified solution (Skarzewski, *Tetrahedron*, 40, 1984, 4997). The synthesis of vitamin K3 from different starting materials like 1-naphthol, 1,4-naphthoquinone was examined using organic oxidizing agents (Rama Rao et al. *Indian J. Chem.* 24 B, 1985, 233).

Oxidation of 2-Methylnaphthalene using hydrogen peroxide in the presence of acid catalysts have been claimed in patents (Sugano et al. Ger. Offen DE. 2341463, 1971; Takanobu et al. Japanese kokai 77, 1977, 108959; Baba et al. Japanese kokai 76, 1976, 50147).

The drawbacks of using inorganic oxidants and mineral acids as given in the referred work are: (i) Catalyst can not be reused, (ii) Disposal of acid is not environmentally safe and it is not economical, (iii) Low selectivity is frequently observed, (iv) Corrosion of the reaction vessel and reactors, (v) Not easy to handle and (vi) High inventory of the catalyst.

OBJECTS OF THE INVENTION

The main object of the present invention is to develop low cost and ecofriendly route for the oxidation of 2-Methylnaphthalene.

Another object of the present invention is to provide a process for the preparation of 2-Methyl-1,4-naphthoquinone.

SUMMARY OF THE INVENTION

Accordingly, the present invention relates to a process for oxidation of 2-Methylnaphthalene with hydrogen peroxide using acetic acid at ambient temperature for at most 3 hours and separating the 2-Methyl-1,4-naphthoquinone from the reaction mixture.

In one embodiment of the invention, the reaction is carried out in the absence of solid catalysts are used.

In another embodiment of the present invention, the reaction is carried out in a temperature range from 60 to 100° C.

In another embodiment of the present invention, the reaction is carried out for a period of 1–3 hrs.

DETAILED DESCRIPTION OF THE INVENTION

The present invention provides a process for oxidation of 2-Methylnaphthalene with hydrogen peroxide in acetic acid. The reaction of the invention avoids the use of solid acid catalysts in the preparation of 2-Methyl-1,4-naphthoquinone.

The following examples are given by the way of illustration and therefore should not be construed as to limit the scope of the present invention.

EXAMPLE 1

20 ml of acetic acid was taken in 50 ml round bottom flask and 1 g of 2-Methylnaphthalene added and kept on a magnetic stirrer. The reaction mixture was heated to 100° C. After reaching 100° C. hydrogen peroxide was added slowly and allowed the reaction mixture for 3 hrs at 100° C. The reaction mixture was analysed using a CHEMITO 8510 Gas Chromatography using 20% SE-30 column coupled with flame ionization detector for product distribution.

A typical Gas Chromatography—Mass spectral fragmentation pattern and Proton Nuclear Magnetic Resonance spectra of the products, $^1$H NMR proves that the product obtained was 2-Methyl-1,4-naphthoquinone. The reaction was carried out using different molar ratios of 2-Methylnaphthalene to hydrogen peroxide (30%) as 1:2, 1:4, 1:6, 1:8 and 1:10. Product was analyzed and the conversion and selectivity are given in Table 1.

TABLE 1

Conversion and selectivities using different molar ratios of 2-methylnaphthalene to hydrogen peroxide (30%)

| Molar ratio of 2-methylnaphthalene to Hydrogen Peroxide | Conversion of 2-Methyl Naphthalene (%) | Selectivity of 2-Methyl-1,4-Naphthoquinone (%) |
| --- | --- | --- |
| 1:2 | 9 | 88 |
| 1:4 | 21 | 90 |
| 1:6 | 42 | 90 |
| 1:8 | 86 | 95 |
| 1:10 | 100 | 100 |

EXAMPLE 2

20 ml of acetic acid was taken in 50 ml round bottom flask and 1 g of 2-Methylnaphthalene added and kept on a magnetic stirrer. The reaction mixture was heated to 100° C. After reaching 100° C. hydrogen peroxide was added slowly and allowed the reaction mixture for 3 hrs at 100° C. The reaction was carried out using 5 to 17 N concentrations of acetic acid. Product was analyzed and the conversion and selectivity are given in Table 2.

TABLE 2

Conversion and selectivities with concentration of acetic acid

| Concentration of acetic acid (N) | Conversion of 2-methyl naphthalene (%) | Selectivity of 2-methyl-1,4-naphthoquinone (%) |
|---|---|---|
| 5 | 35 | 91 |
| 10 | 75 | 100 |
| 17 | 100 | 100 |

EXAMPLE 3

20 ml of acetic acid was taken in 50 ml round bottom flask and 1 g of 2-Methylnaphthalene added and kept on a magnetic stirrer. The reaction mixture was heated to 100° C. After reaching 100° C., hydrogen peroxide was added slowly and allowed the reaction mixture for 3 hrs at 100° C. The reaction was carried out using 10 to 50% concentration of hydrogen peroxide. Product was analyzed and the conversion and selectivity are given in the Table 3.

TABLE 3

Conversion and selectivities with concentration of hydrogen peroxide

| Concentration of Hydrogen peroxide (%) | Conversion of 2-methyl Naphthalene (%) | Selectivity (%) | |
|---|---|---|---|
| | | 2-methyl-1,4-naphthoquinone | 6-methyl-1,4-naphthoquinone |
| 10 | 55 | 97 | — |
| 20 | 66 | 97 | — |
| 30 | 100 | 100 | — |
| 50 | 75 | 87 | 13 |

EXAMPLE 4

20 ml of acetic acid was taken in 50 ml round bottom flask and 1 g of 2-Methylnaphthalene added and kept on a magnetic stirrer. The reaction mixture was heated to 100° C. After reaching 100° C. hydrogen peroxide was added slowly and allowed the reaction mixture for heating at 100° C. The reaction was carried out for different time periods ranging from 30 min to 240 min. Products were analyzed and the conversion and selectivity are given in the Table 4.

TABLE 4

Conversion and selectivities with the variation in the time

| Reaction time (min) | Conversion of 2-methyl Naphthalene (%) | Selectivity (%) | |
|---|---|---|---|
| | | 2-methyl-1,4-naphthoquinone | 6-methyl-1,4-naphthoquinone |
| 30 | 48 | 100 | — |
| 60 | 87 | 100 | — |
| 90 | 86 | 100 | — |
| 120 | 95 | 100 | — |
| 150 | 96 | 100 | — |
| 180 | 100 | 100 | — |
| 240 | 91 | 90 | 10 |

EXAMPLE 5

1 g of 2-Methylnaphthalene taken in 50 ml round bottom flask and acetic acid was added and was kept on a magnetic stirrer. The reaction mixture was heated to 100° C. After reaching 100° C. hydrogen peroxide was added slowly and allowed the reaction mixture for 3 hrs at 100° C. The reaction was carried out by changing the amount of acetic acid from 5 to 20 ml. Product was analyzed and the conversion and selectivity are given in the Table 5.

TABLE 5

Conversion and selectivities changing the amount of acetic acid

| Acetic Acid (ml) | Conversion of 2-methylnaphthalene (%) | Selectivity of 2-methyl-1,4-naphthoquinone (%) |
|---|---|---|
| 5 | 0 | 0 |
| 10 | 24 | 100 |
| 15 | 89 | 100 |
| 20 | 100 | 100 |

EXAMPLE 6

20 ml of acetic acid was taken in 50 ml round bottom flask and 1 g of 2-Methylnaphthalene added and kept on a magnetic stirrer and hydrogen peroxide was added slowly and allowed the reaction mixture for 3 hrs while stirring. The reaction was carried out by varying the reaction temperature from 40 to 100° C. Product was analyzed and the conversion and selectivities are given in the Table 6.

TABLE 6

Conversion and selectivities with reaction temperature

| Reaction temperature (° C.) | Conversion of 2-methylnaphthalene (%) | Selectivity of 2-methyl-1,4-naphthoquinone (%) |
|---|---|---|
| 40 | 7 | 100 |
| 60 | 40 | 100 |
| 80 | 52 | 100 |
| 100 | 100 | 100 |

The main advantages of the present invention are: oxidation of 2-Methylnaphthalene to 2-Methyl-1,4-naphthoquinone with hydrogen peroxide in acetic acid without the use of solid catalyst is being reported for the first time. Also, this method provides the following advantages compared with the conventional process (i) high conversion and selectivity are frequently observed, (iii no waste is produced which is an ecofriendly process, (iii) do not corrode reaction vessel or reactors and (iv) it is a very economical process as there is no involvement of solid catalysts.

In view of the above, it will be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

We claim:

1. A process for the preparation of 2-Methyl,1,4-naphthoquinone, said process comprising the steps of:
   a) oxidising 2-methylnaphthalene with hydrogen peroxide in the presence of 5N to 17N acetic acid for 1 to 3 to three hours in the absence of a solid catalyst wherein the molar ration of 2-methynaphthalene to hydrogen peroxide is in the range of 1:2 to 1:12 and
   b) separating the 2-methyl-1, 4-naphthoquinone so obtained.

2. A process as claimed in claim 1 wherein the temperature is in the range of 60–100° C.

* * * * *